(12) United States Patent
Newbold et al.

(10) Patent No.: US 10,898,677 B2
(45) Date of Patent: Jan. 26, 2021

(54) VENTED GUIDEWIRE RETAINER AND RELATED METHODS

(71) Applicant: Merit Medical Systems, Inc., South Jordan, UT (US)

(72) Inventors: Steven Newbold, West Jordan, UT (US); Neil Peterson, Highland, UT (US); Jason Reber, Woods Cross, UT (US); Keith Denney, Lehi, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 352 days.

(21) Appl. No.: 15/633,006

(22) Filed: Jun. 26, 2017

(65) Prior Publication Data
US 2017/0368301 A1 Dec. 28, 2017

Related U.S. Application Data

(60) Provisional application No. 62/355,729, filed on Jun. 28, 2016.

(51) Int. Cl.
*A61M 25/00* (2006.01)
*A61M 25/09* (2006.01)

(52) U.S. Cl.
CPC .......... *A61M 25/002* (2013.01); *A61M 25/09* (2013.01); *A61M 25/09041* (2013.01); *A61M 2025/0079* (2013.01)

(58) Field of Classification Search
CPC .......... A61M 25/09041; A61M 25/002; A61M 25/09; A61M 2025/0079; A61M 2025/00079; A61L 2/20; A61L 2202/24; B65H 75/364
See application file for complete search history.

(56) References Cited

U.S. PATENT DOCUMENTS

| | | | | |
|---|---|---|---|---|
| 1,816,301 | A | * 7/1931 | Sundell | F16B 2/245 24/339 |
| 3,633,758 | A | * 1/1972 | Morse | A61M 25/002 211/85.13 |
| 4,361,380 | A | 11/1982 | Marazzi | |

(Continued)

FOREIGN PATENT DOCUMENTS

| EP | 0587984 | 3/1994 |
|---|---|---|
| JP | 2014144132 | 8/2014 |

OTHER PUBLICATIONS

International Search Report and Written Opinion dated Sep. 13, 2017 for PCT/US2017/39248.

(Continued)

*Primary Examiner* — Tiffany Legette
(74) *Attorney, Agent, or Firm* — Stoel Rives LLP

(57) ABSTRACT

A guidewire retention assembly is disclosed. The assembly may include a body member extending between a first end and a second end and defining a retention lumen, a connector defining a connector lumen, a vent, and a continuous outside surface, the vent comprising an opening extending radially from the connector lumen, and the connector releasably coupleable to the first end of the body member and the second end of the body member, such that the connector releasably couples the first end of the body member to the second end of the body member.

12 Claims, 8 Drawing Sheets

(56) References Cited

U.S. PATENT DOCUMENTS

| | | | | |
|---|---|---|---|---|
| 4,750,803 | A * | 6/1988 | Schmidt | G02B 6/3874 |
| | | | | 385/72 |
| 4,781,704 | A * | 11/1988 | Potter | A61J 15/0003 |
| | | | | 604/105 |
| 5,125,906 | A | 6/1992 | Fleck | |
| 5,219,332 | A * | 6/1993 | Nelson | A61B 17/22 |
| | | | | 600/434 |
| 5,344,011 | A | 9/1994 | Dibernardo et al. | |
| 5,472,081 | A * | 12/1995 | Kilgrow | A61B 17/06133 |
| | | | | 206/382 |
| 5,503,266 | A * | 4/1996 | Kalbfeld | A61B 17/06133 |
| | | | | 206/380 |
| 5,507,300 | A * | 4/1996 | Mukai | A61M 25/09041 |
| | | | | 600/585 |
| 5,703,982 | A * | 12/1997 | Takizawa | G02B 6/3869 |
| | | | | 385/60 |
| 5,947,925 | A * | 9/1999 | Ashiya | A61M 25/0169 |
| | | | | 604/164.08 |
| 6,047,825 | A * | 4/2000 | Samuels | A61M 25/002 |
| | | | | 206/364 |
| 6,162,395 | A | 12/2000 | Kowanko | |
| 6,375,006 | B1 * | 4/2002 | Samuels | A61M 25/002 |
| | | | | 206/210 |
| 6,431,219 | B1 * | 8/2002 | Redler | A61L 29/085 |
| | | | | 138/137 |
| 6,588,588 | B2 * | 7/2003 | Samuels | A61M 25/002 |
| | | | | 206/364 |
| 7,757,691 | B2 * | 7/2010 | Reynolds | A61B 17/0057 |
| | | | | 128/207.15 |
| 8,931,637 | B2 * | 1/2015 | Deeds | A61M 25/002 |
| | | | | 206/364 |
| 8,974,419 | B2 * | 3/2015 | Silva | A61M 25/0021 |
| | | | | 604/160 |
| 9,821,140 | B2 * | 11/2017 | Pini | A61M 25/0023 |
| 2002/0144920 | A1 * | 10/2002 | Samuels | A61M 25/002 |
| | | | | 206/364 |
| 2005/0054953 | A1 | 3/2005 | Ryan et al. | |
| 2005/0061698 | A1 | 3/2005 | Delaney et al. | |
| 2008/0257441 | A1 * | 10/2008 | Allen | A61L 29/041 |
| | | | | 138/137 |
| 2015/0038923 | A1 * | 2/2015 | Byrnes | A61L 29/126 |
| | | | | 604/265 |

OTHER PUBLICATIONS

European Search Report dated Jan. 27, 2020 for EP17821004.3.
European Search Report dated Jun. 25, 2020 for EP17821004.3.

* cited by examiner

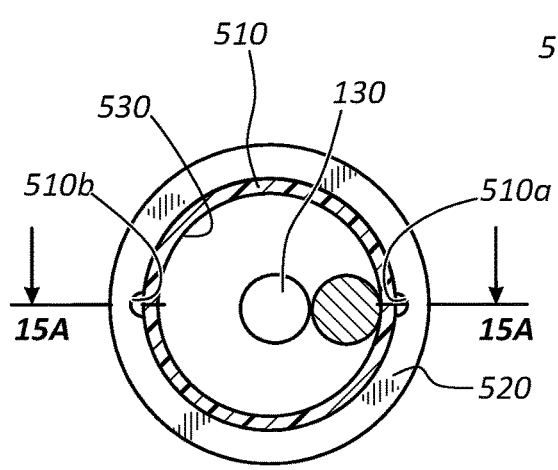
FIG. 13
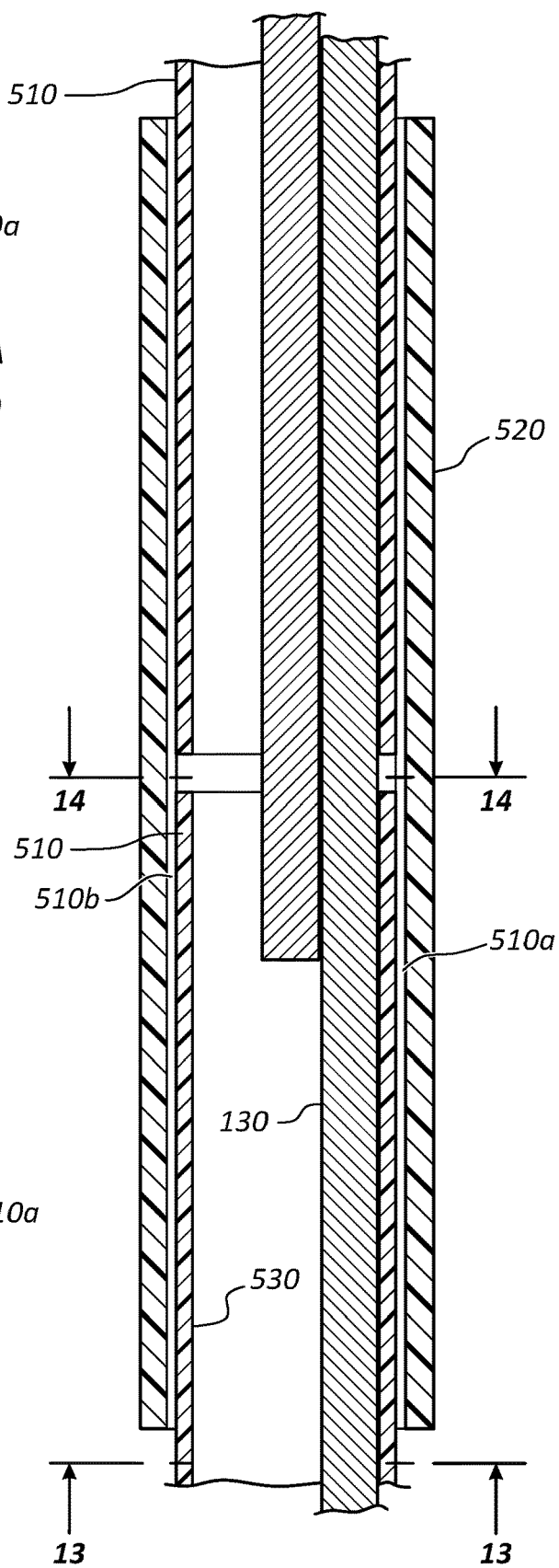
FIG. 14
FIG. 15A

VENTED GUIDEWIRE RETAINER AND RELATED METHODS

RELATED APPLICATIONS

This application claims priority to U.S. Provisional Application No. 62/355,729 filed on Jun. 28, 2016 and titled "Vented Guidewire Retainer and Related Methods" which is hereby incorporated by reference in its entirety.

TECHNICAL FIELD

The present disclosure relates generally to guidewire retention assemblies. More particularly, some embodiments relate to a guidewire retention assembly with a body member and a connector with a vent to connect the two ends of the body member together to retain a guidewire.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 13 is a cross-section view of a guidewire retention assembly according to some embodiments, taken through a cross sectional plane shown as line 13-13 of FIG. 15.

FIG. 14 is a cross-section view of the guidewire retention assembly of FIG. 13 taken through line 14-14 of FIG. 15.

FIG. 15A is a cross-section view of the guidewire retention assembly of FIG. 13 taken through the line 15A-15A of FIG. 13.

DETAILED DESCRIPTION

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical and fluidic interaction. Thus, two components may be coupled to each other even though they are not in direct contact with each other. The phrases "attached to" or "attached directly to" refer to interaction between two or more entities which are in direct contact with each other and/or are separated from each other only by a fastener of any suitable variety (e.g., an adhesive). The phrase "fluid communication" is broad enough to refer to arrangements in which a fluid (e.g., a gas or a liquid) can flow from one element to another element when the elements are in fluid communication with each other.

"Fluid" is used in its broadest sense, to refer to any fluid, including both liquids and gasses, as well as solutions, compounds, suspensions, etc., which generally behave as a fluid.

Figure 1:
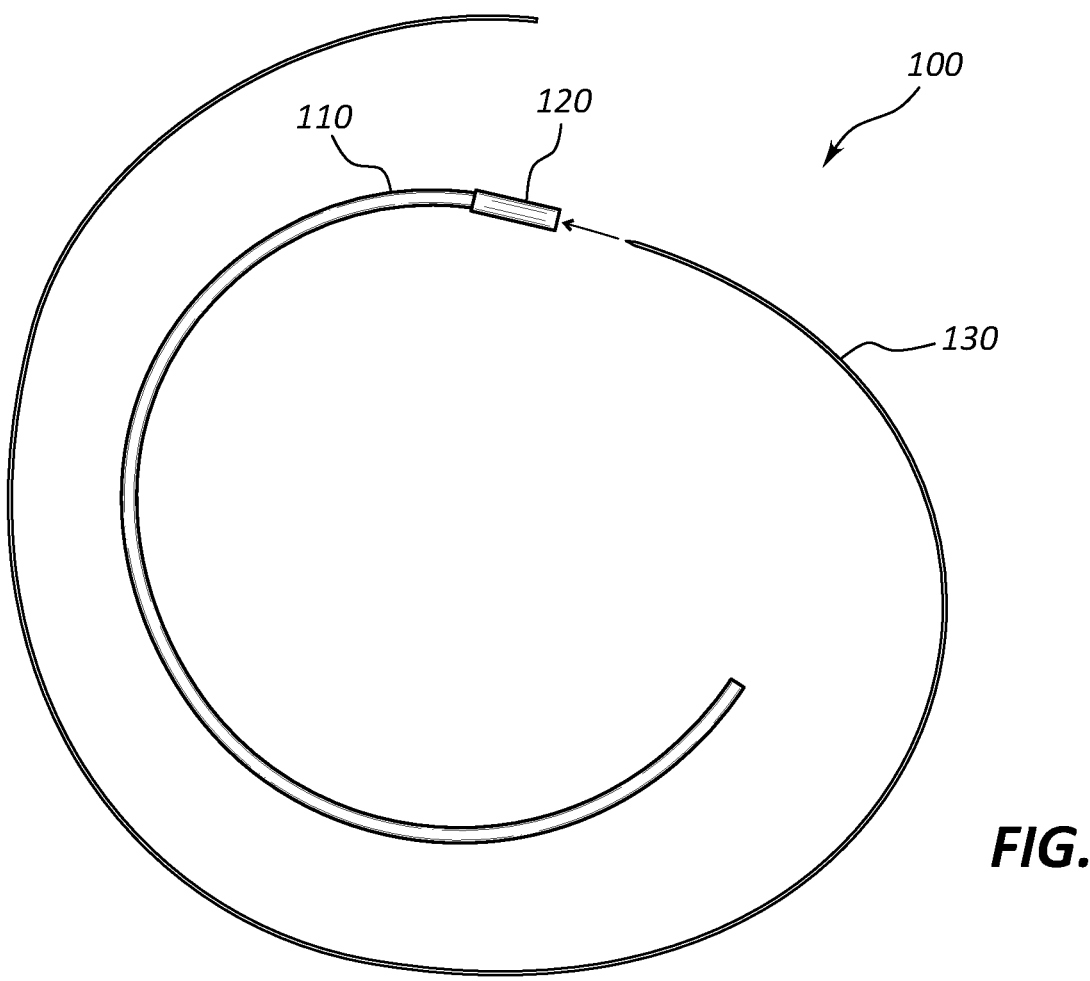
FIG. 1 is a top view of an unassembled guidewire retention assembly comprising a connector, a body member, and a guidewire.
Figure 4:
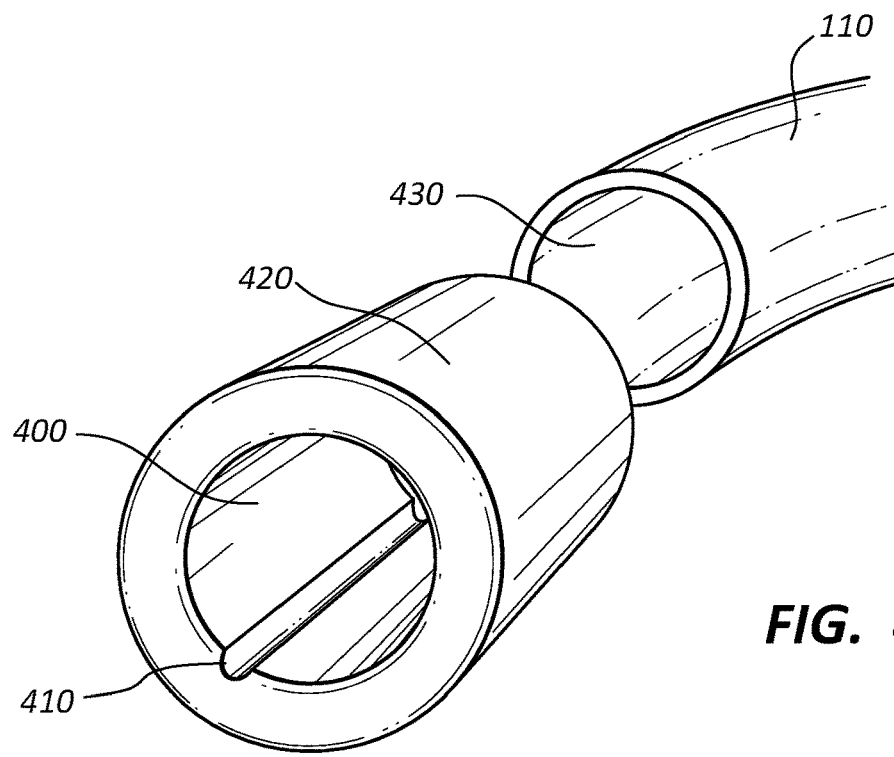
FIG. 4 is a perspective view of the connector and one end of the body member of FIG. 1.

FIG. 1 is a top view of an unassembled guidewire retention assembly 100. The guidewire retention assembly 100 includes a body member 110, a connector 120, and a guidewire 130. Body member 110 extends between a first end and a second end. The body member 110 is hollow and defines a retention lumen 430 to retain the guidewire 130, as seen in FIG. 4.

A guidewire 130 is positioned in the guidewire retention assembly 100 for packaging and sterilization prior to use, as will be discussed in more detail below. When the guidewire 130 is ready for use in a medical application, a user may remove the sanitized guidewire 130 from the guidewire retention assembly 100.

As can be seen in FIG. 1, to position the guidewire 130 into the retention lumen 430 of the body member 110, one end of the body member 110 is disconnected from the connector 120 and the guidewire 130 is fed into the body member 110 through the connector 120, as seen in FIG. 1.

Figure 2:
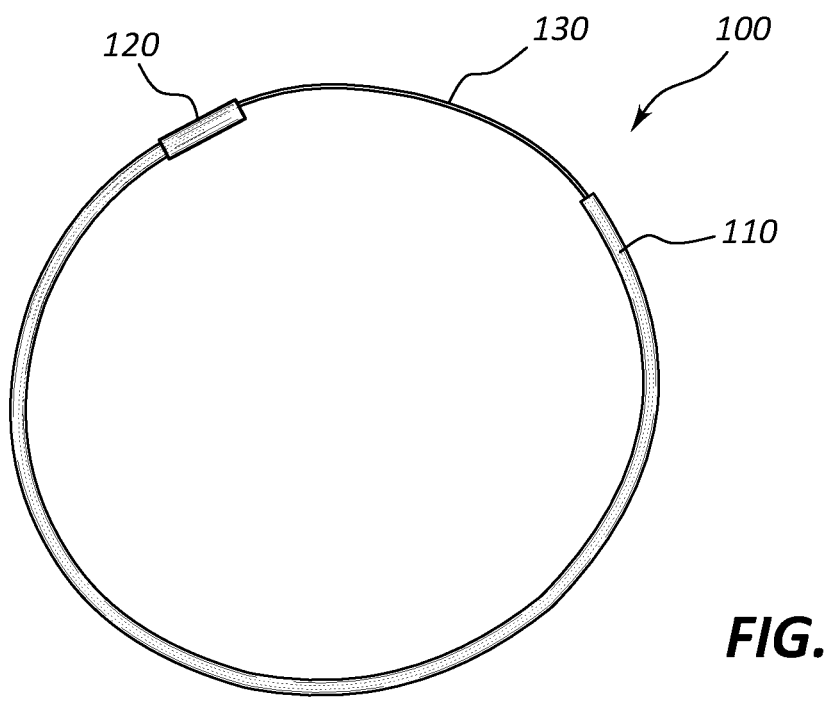
FIG. 2 is a top view of the guidewire retention assembly of FIG. 1 partially assembled.
Figure 3:
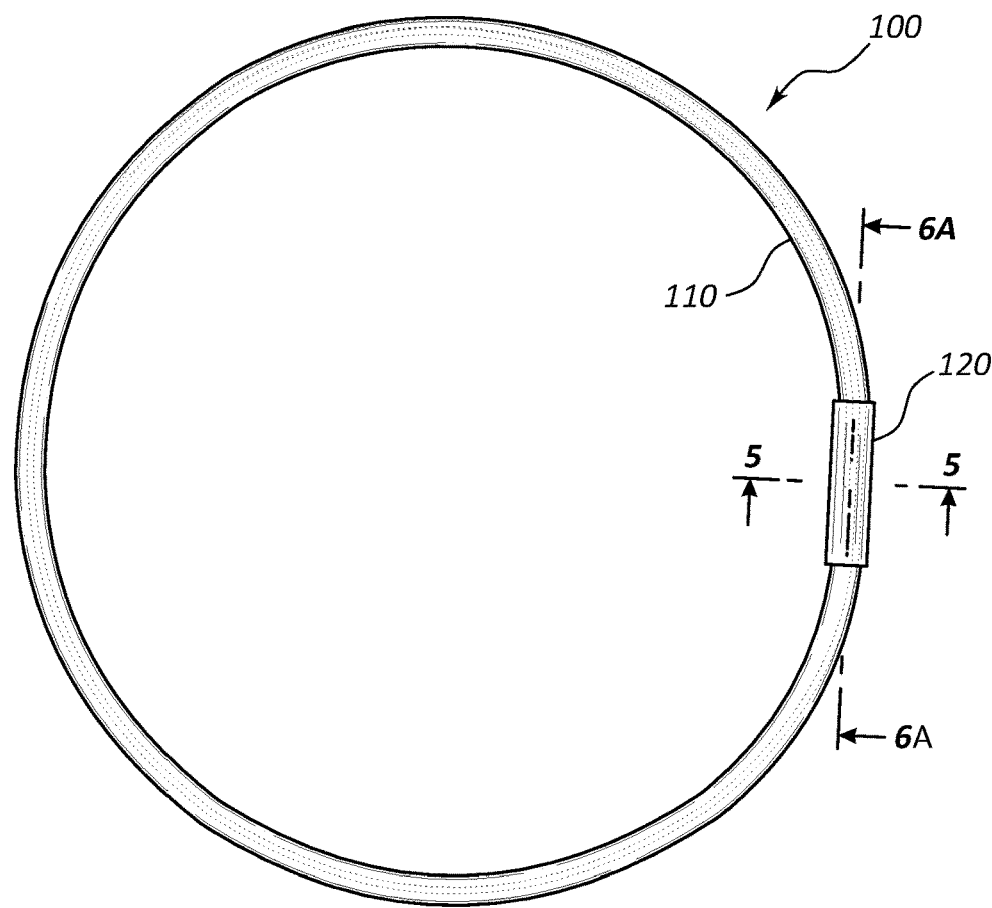
FIG. 3 is another top view of the guidewire retention assembly of FIG. 1 fully assembled.

FIG. 2 is a top view of the guidewire retention assembly 100 partially assembled. The guidewire 130 may be longer than the body member 110, as shown in FIG. 1. In such a case, the guidewire 130 overlaps in the connector 120 and body member 110 until the second end of the body member 110 can be connected to the connector 120, as shown in FIG. 3. That is, the retention lumen 430 of the body member 110 is a large enough diameter for the guidewire 130 to be overlapped inside of the retention lumen 430. This allows the guidewire 130 to fit inside the retention lumen 430 of the body member 110, even if the guidewire 130 is longer than the body member 110.

The connector 120 is shown in more detail in FIG. 4. In the illustrated embodiment, the connector 120 has a continuous outer surface 420. That is, the outer surface 420 of the connector 120 does not contain any holes or vents. The connector 120 includes a hollow interior defining a connector lumen 400. The connector 120 also includes a vent 410 that extends radially from the connector lumen 400. The vent 410 may comprise a trough that extends longitudinally along the entire length of the connector lumen 400.

As seen in FIGS. 1-4, the ends of the body member 110 are sized such that they are disposable with the connector lumen 400 of the connector 120. This allows the ends of the body member 110 to connect and provide a housing for the guidewire 130. Preferably, the ends of the body member 110 are slightly less in diameter than the connector lumen 400 so that the body member 110 fits tightly in the connector lumen 400, but can still be removed to gain access to the retention lumen 430. Thus, the ends of the body member 110 may be releasably coupled to the connector 120.

Figure 5:
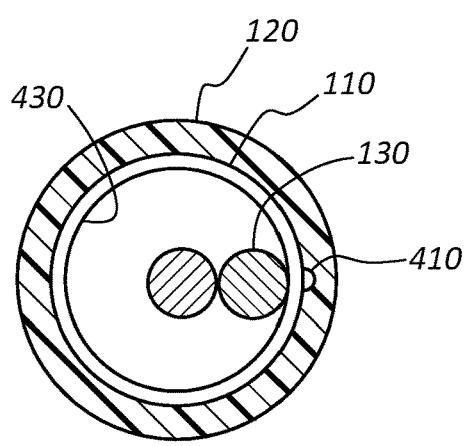
FIG. 5 is a cross-section view of the guidewire retention assembly of FIG. 3, taken through the line 5-5 as indicated in FIG. 3.

FIG. 5 illustrates a cross-sectional view of the connector 120, body member 110 and guidewire 130, taken along the line 5-5 in FIG. 3. This cross-sectional view shows the ends of body member 110 sized to fit within the connector 120. The vent 410 included in the connector 120 is also shown. The guidewire 130 is overlapped in the retention lumen 430 of the body member 110 due to the guidewire 130 being longer than the body member 110.

Figure 6A:
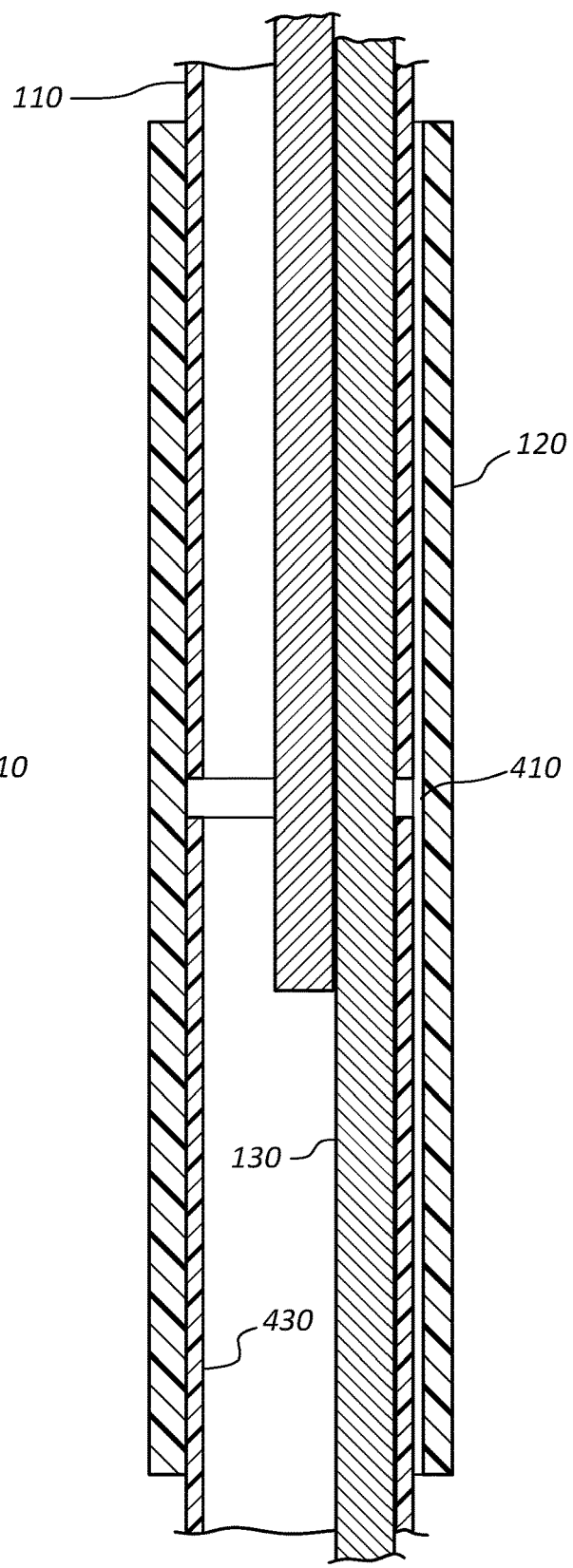
FIG. 6A is a cross-section view of the guidewire retention assembly of FIG. 3, taken through the line 6A-6A as indicated in FIG. 3.
Figure 6B:
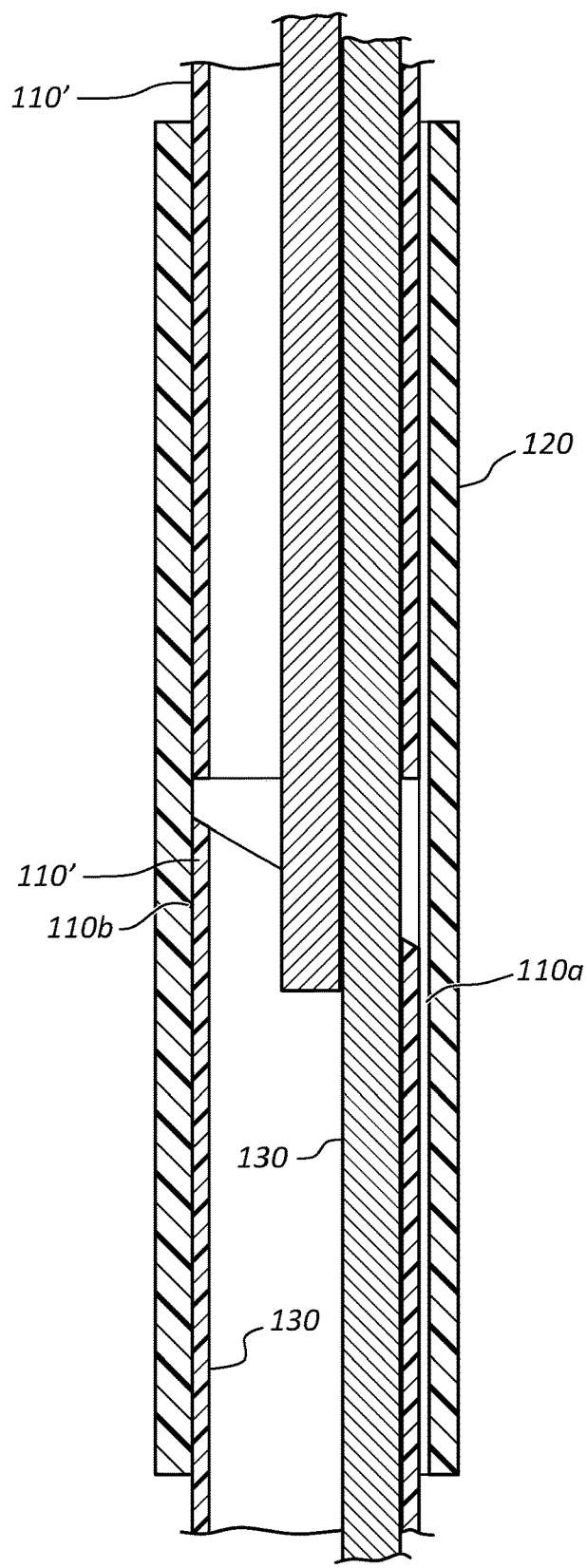
FIG. 6B is a cross-section view of a guidewire retention assembly according to some embodiments.

FIG. 6A shows another cross-section view of the connector 120, body member 110, and guidewire 130, taken along the line 6-6 in FIG. 3. As can also be see in FIG. 6, the ends of the body member 110 are sized to fit within connector 120. The guidewire 130 overlaps to fit within the body member 110 and connector 120. In FIG. 6A, the vent 410 can be seen below the guidewire 130.

In the assembled configuration, such as shown in FIG. 3, the vent 410 provides a fluid pathway between an exterior environment and the retention lumen 430 of the body member 110. In other words, the vent 410 may be in fluid communication with retention lumen 430 of the body member 110 when the ends of the body member 110 are coupled to the connector 120, as seen in FIG. 6A. As seen in FIG. 6A, the ends of the body member 110 may not seal against each other in the connector 120. This allows the vent 410 to be in fluid communication with the retention lumen 430. Stated another way, a fluid can flow through vent 410 to the connector lumen 400 and then into the retention lumen 430.

In some embodiments, the ends of the body member 110 may directly abut each other while still providing fluid communication between the vent 410 and the retention lumen 430. For example, in FIG. 6B, at least one end of the body member 110' may be angled to provide an opening for fluid to enter the retention lumen 430 even if portions of the ends of the body member 110' directly abut each other.

When the guidewire retention assembly is assembled, as shown in FIG. 3, for example, fluid in an external environment around the connector 120 may diffuse or otherwise travel through the vent 410 to the retention lumen 430 of the body member 110. The fluid may be, for example, a sterilization gas to sterilize the guidewire 130 prior to use in a medical procedure. The sterilization gas may flow through the vent 410 of connector 120 into the retention lumen 430 of the body member 110. The guidewire 130 may thus be exposed to the sterilization gas in the retention lumen 430 of the body member 110. This allows the guidewire 130 to be packaged in the guidewire retention assembly 100 prior to being sterilized. Therefore, when the guidewire 130 is removed from the guidewire retention assembly 100 for use in a medical procedure, the guidewire 130 may be fully sterilized. The connector 120 and vent 410 may be formed as a single unit during manufacture, such as by extruding a single piece of material having a cross-section such as shown in FIG. 5. Forming the connector 120 and vent 410 in this way may thus avoid the necessity of creating a vent by modifying the connector 120 after manufacture, such a drilling a hole in the connector, to provide a vent for sterilization gas to flow through.

Figure 7:
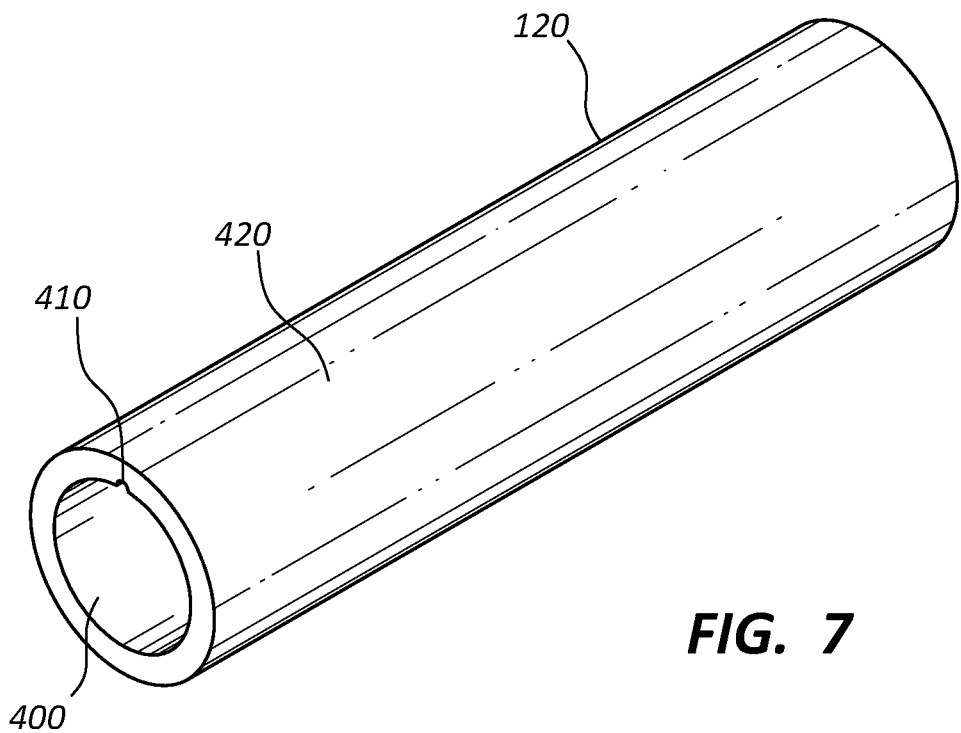
FIG. 7 is a perspective view of the connector of FIG. 1.
Figure 8:
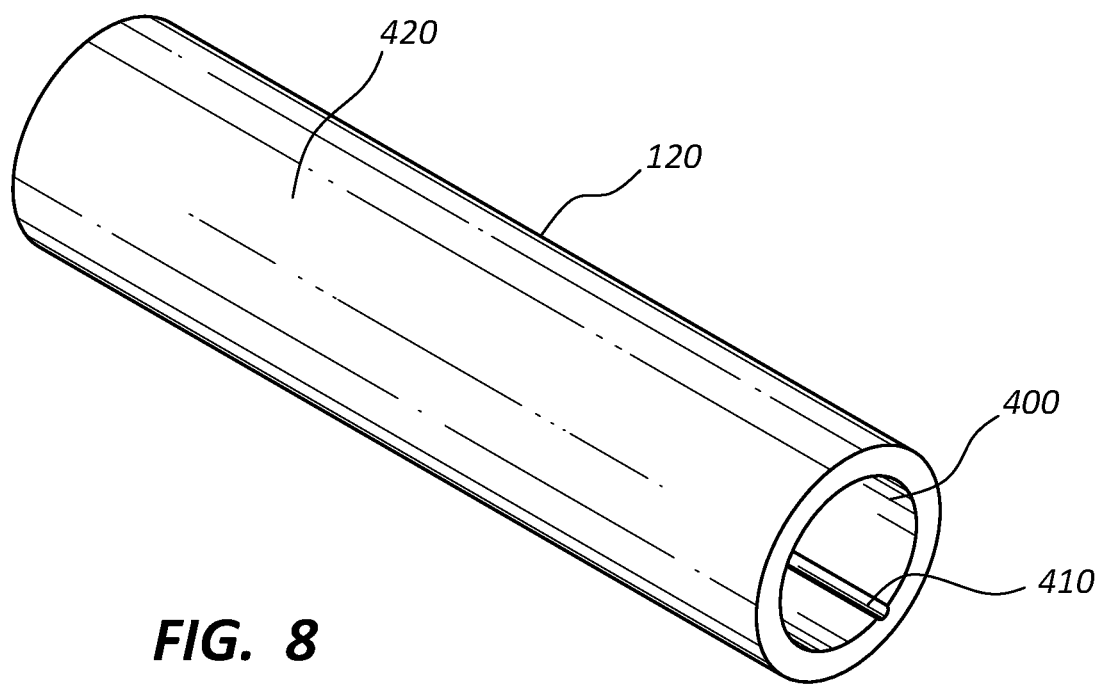
FIG. 8 is another perspective view of the connector of FIG. 1.
Figure 9:
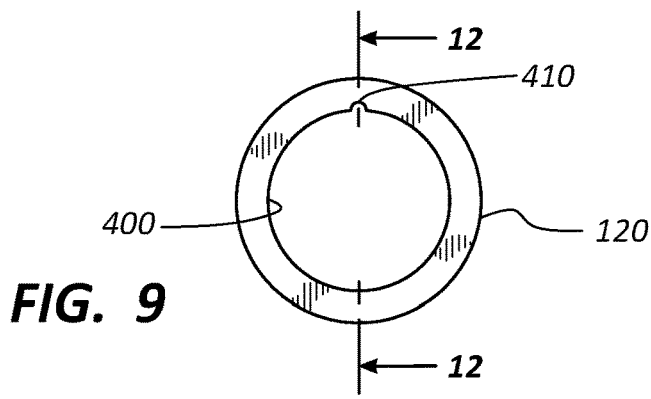
FIG. 9 is a front view of the connector of FIG. 1.
Figure 10:
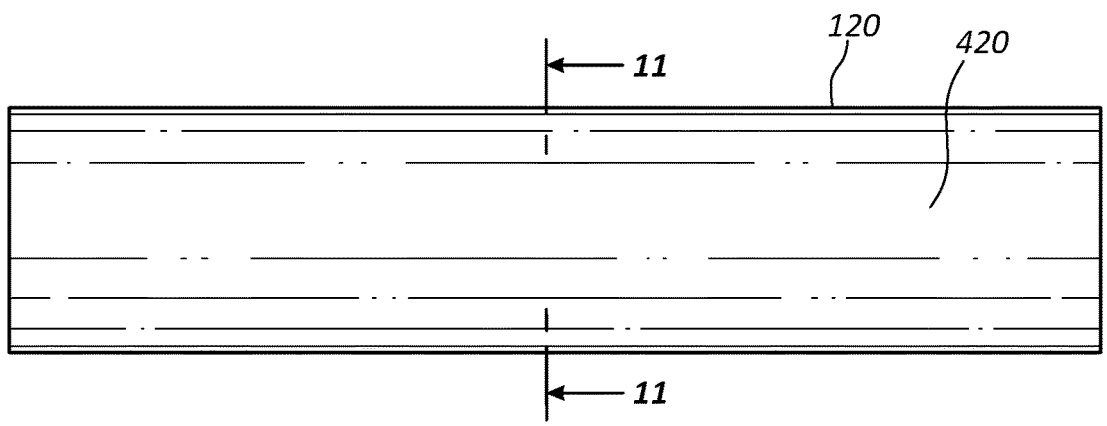
FIG. 10 is another side view of the connector of FIG. 1.
Figure 11:
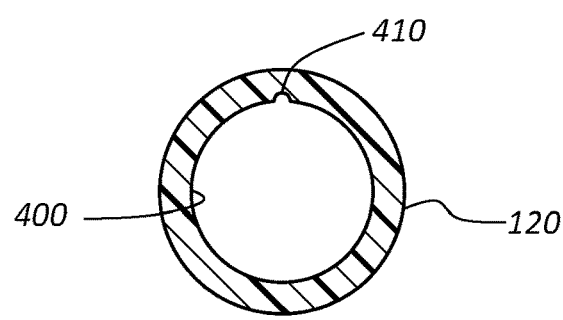
FIG. 11 is a cross-section view of the connector of FIG. 1, taken through the line 11-11 as indicated in FIG. 10.
Figure 12:
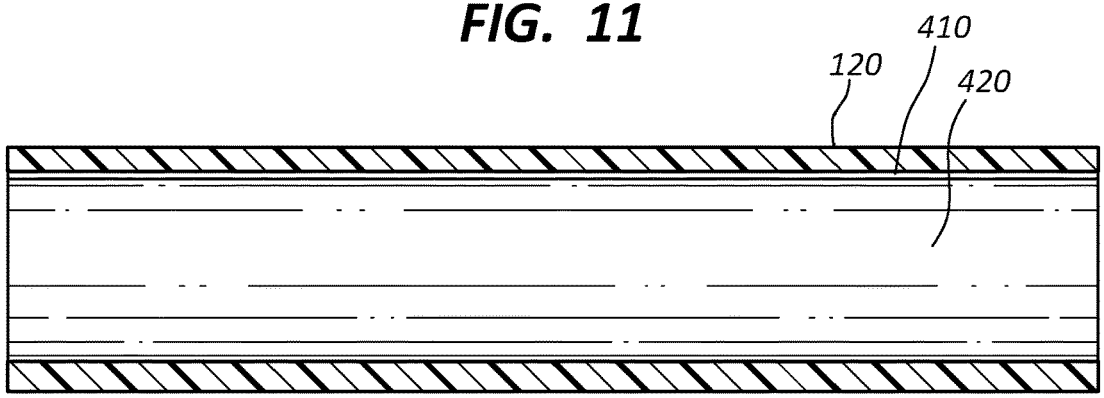
FIG. 12 is a cross-section view of the connector of FIG. 1, taken through the line 12-12 as indicated in FIG. 9.

FIGS. 7 through 12 show various views of the connector 120 with the vent 410 provided within the connector 120. FIGS. 7 and 8 illustrate side views of the connector 120 with vent 420 extending radially from the connector lumen 400 across the entirety of the connector lumen 400. FIG. 9 illustrates a front view of one end of the connector 120 and vent 410. FIG. 10 illustrates a side view of the connector 120. FIG. 11 illustrates a cross-section view of the connector 120 taken through the line 11-11 in FIG. 10, while FIG. 12 illustrates a cross-section view of the connector 120 and vent 410 taken through the line 12-12 in FIG. 9. As shown in these views, the connector 120 may comprise a round exterior shape, and may be radially symmetric, such that any side view, a top view, and a bottom view are all identical.

In some embodiments, the connector may contain multiple vents to allow fluid in an external environment around the connector to diffuse or otherwise travel through the vents to the retention lumen of the body member. FIGS. 13-15a illustrate a connector with two vents. FIGS. 13 and 14 show a cross-section view taken through line 13-13 and line 14-14, respectively, of FIG. 15a of body member 510. FIGS. 13 and 14 show body member 510 within connector 520. The guidewire 130 is located in the retention lumen 530 of the body member 510, similar to other embodiments discussed above. Rather than defining a single vent 410, as shown in FIG. 4, the connector 520 defines two vents 510a and 510b. The two vents 510a and 510b may be offset by 180 degrees from each other, as shown in FIGS. 13 and 14. However, the embodiments are not limited to a 180 degree separation between the vents. The vents 510a and 510b may be placed anywhere along the connector lumen. Vents 510a and 510b extend radially from the connector lumen, similar to vent 410 discussed above. The vents 510a and 510b may comprise troughs that extends longitudinally along the entire length of the connector lumen. Further, although two vents are shown in FIGS. 13-15A-B, any number of vents, for example, three, four, five, six, or more vents, may be defined by the connector 120 or 520.

Similar to FIG. 6A discussed above, FIG. 15A shows another cross-section view of the connector 520, body member 510, and guidewire 130, taken along the line 15A-15A in FIG. 3. As can also be see in FIG. 15A, the ends of the body member 110 are sized to fit within connector 120. The guidewire 130 overlaps to fit within the body member 510 and connector 520. In this embodiment, the vents 510a and 510b are each in fluid communication with the retention lumen 530.

Figure 15B:
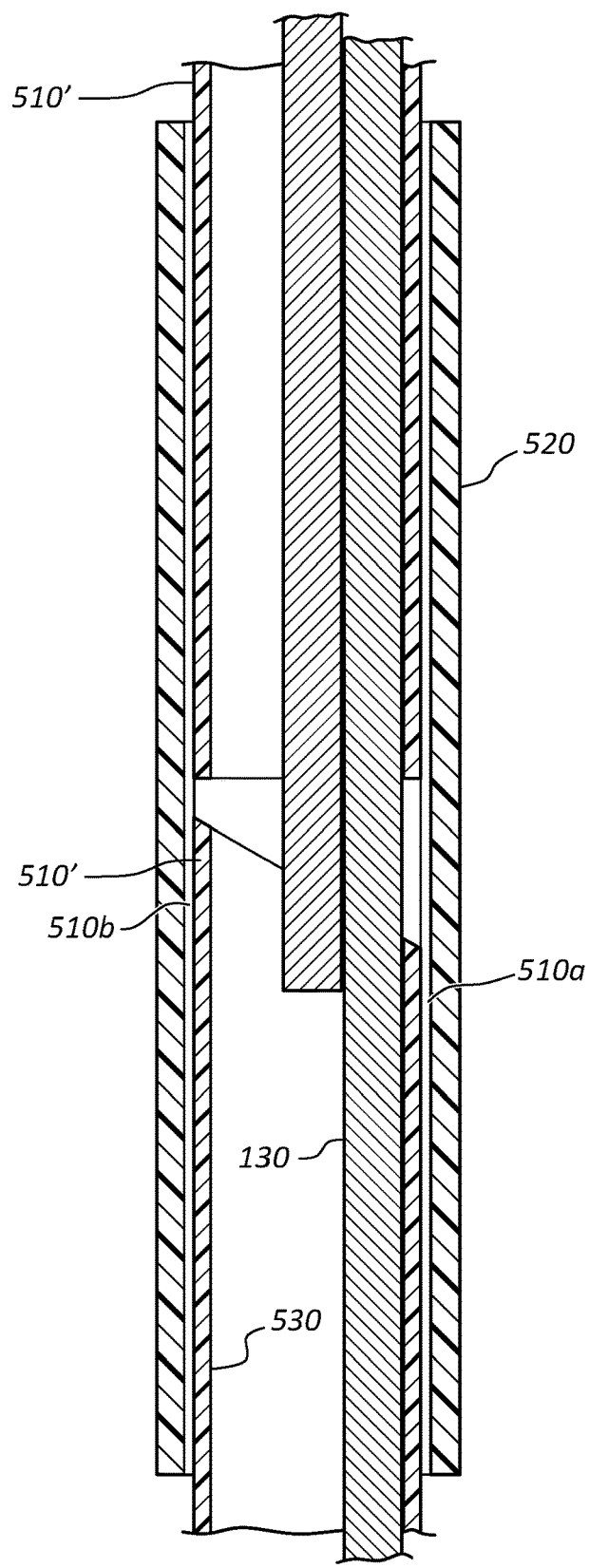
FIG. 15B is a cross-section view of a guidewire retention assembly according to some embodiments.

In some embodiments, as shown in FIG. 15B, at least one end of the body member 510' may be angled to allow fluid to enter the retention lumen 530 even if portions of the ends of the body member 510' directly abut each other. Additionally, in embodiments wherein two vents (such as 510a and 510b) are disposed at 180 degrees to each other, at least one vent will be in direct communication with the gap created by the angled end of the body member 510', even if the opposite vent directly aligns with the portions of the ends of the body member 510' that may directly abut each other.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A guidewire retention assembly comprising: a body member comprising a first end and a second end and defining a retention lumen therebetween; a connector defining a connector lumen, a vent, and a continuous outside surface, the vent extending radially from the connector lumen; and the connector releasably coupleable to the first end of the body member and the second end of the body member, such that the connector releasably couples the first end of the body member to the second end of the body member, wherein the continuous outside surface extends entirely around the connector lumen and is continuous such that the continuous outside surface does not contain an opening, and wherein the vent extends longitudinally along an entire length of the connector lumen.

2. The guidewire retention assembly of claim 1, wherein the vent comprises a longitudinally extending trough.

3. The guidewire retention assembly of claim 1, wherein the vent is in fluid communication with an exterior environment at a first end of the connector and at a second end of the connector.

4. The guidewire retention assembly of claim 1, wherein the connector further defines a plurality of vents.

5. The guidewire retention assembly of claim 1, wherein the first end of the body member is angled.

6. The guidewire retention assembly of claim 1, wherein the vent is in fluid communication with the retention lumen when the first end of the body member and the second end of the body member are coupled to the connector.

7. The guidewire retention assembly of claim 6, wherein the vent defines a fluid pathway between an exterior environment and the retention lumen when the first end of the body member and the second end of the body member are coupled to the connector.

8. The guidewire retention assembly of claim 1, wherein the vent is a first vent, and wherein the connector further defines a second vent separated from the first vent.

9. The guidewire retention assembly of claim 8, wherein the second vent is positioned from the first vent by 180 degrees.

10. A guidewire retention assembly comprising: a body member comprising a first end and a second end and defining a retention lumen therebetween, the body member comprising an outside surface; a connector releasably coupleable to the first end of the body member and the second end of the body member, such that the connector releasably couples the first end of the body member to the second end of the body member, the connector comprising a first end, a second end opposite the first end, a vent extending radially from a connector lumen and an inside surface; and a fluid pathway disposed between the outside surface of the body member and the inside surface of the connector, wherein the fluid pathway extends longitudinally along an entire length of the connector, and wherein the vent extends longitudinally along an entire length of the connector lumen.

11. The guidewire retention assembly of claim 10, wherein the fluid pathway is in fluid communication with the retention lumen when the first end of the body member and the second end of the body member are coupled to the connector.

12. The guidewire retention assembly of claim 10, wherein the fluid pathway is at least partially defined by the outside surface of the body member and the inside surface of the connector.

* * * * *